United States Patent [19] [11] 4,443,368
Sherwood et al. [45] Apr. 17, 1984

[54] PEPTIDES AFFECTING GONADAL FUNCTION

[75] Inventors: Nancy M. Sherwood, Victoria, Canada; Lee E. Eiden; Michael J. Brownstein, both of Bethesda, Md.; Joachim Spiess, Encinitas, Calif.; Jean E. F. Rivier; Wylie W. Vale, Jr., both of La Jolla, Calif.

[73] Assignee: The Salk Institute for Biological Studies, San Diego, Calif.

[21] Appl. No.: 437,949

[22] Filed: Nov. 1, 1982

[51] Int. Cl.$^3$ ............................................ C07C 103/52
[52] U.S. Cl. ........................................... 260/112.5 LH
[58] Field of Search ................. 424/177; 260/112.5 R, 260/112.5 LH

[56] References Cited

U.S. PATENT DOCUMENTS

| | | | |
|---|---|---|---|
| 3,992,365 | 11/1976 | Beddell et al. | 260/112.5 LH |
| 4,003,884 | 1/1977 | König et al. | 260/112.5 LH |
| 4,075,191 | 2/1978 | Beddell et al. | 260/112.5 LH |
| 4,083,967 | 4/1978 | Beddell et al. | 260/112.5 LH |
| 4,086,219 | 4/1978 | Wittle et al. | 424/177 |
| 4,111,923 | 9/1978 | Wittle et al. | 424/177 |
| 4,118,483 | 10/1978 | König et al. | 424/177 |

FOREIGN PATENT DOCUMENTS 21620  1/1981  European Pat. Off. .

OTHER PUBLICATIONS

Fujino et al., *Biochemical and Biophysical Research Communications*, 60, No. 1, 406–340, (1974).
Coy et al., *Biochemical and Biophysical Research Communications*, 57, No. 2, 335–340, (1974).

*Primary Examiner*—Delbert R. Phillips
*Assistant Examiner*—F. T. Moezie
*Attorney, Agent, or Firm*—Fitch, Even, Tabin & Flannery

[57] ABSTRACT

The peptide having the following formula has a potent effect on the reproduction processes of fish and is termed Fish GnRH:

pGlu-His-Trp-Ser-Tyr-Gly-Trp-Leu-Pro-Gly-NH$_2$.

Spawning of teleostei fish can be promoted by administration of effective amounts of the peptide.

7 Claims, No Drawings

PEPTIDES AFFECTING GONADAL FUNCTION

This invention was made with Government support under Grant No. HD-13527 awarded by the Department of Health and Human Services (NIH). The Government has certain rights in this invention. The present invention relates to peptides which influence the release of gonadotropins by the pituitary gland in fish. More particularly, the present invention is directed to a peptide which when administered to fish exhibits potency in releasing gonadotropins and in causing spawning.

BACKGROUND OF THE INVENTION

The pituitary gland is attached to a stalk to the region in the base of the brain known as the hypothalamus and has two principal lobes, the anterior lobe and the posterior lobe. The posterior lobe of the pituitary gland stores and passes onto the general circulation system two hormones manufactured in the hypothalamus, i.e., vasopressin and oxytocin. The anterior lobe of the pituitary gland secretes a number of hormones, which are complex protein or glycoprotein molecules, that travel through the blood stream to various organs and which, in turn, stimulate the secretion into the blood stream of other hormones from the peripheral organs. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and also regulate the production and maturation of gametes.

The release of a hormone by the anterior lobe of the pituitary gland usually requires a prior release of another class of hormones produced by the hypothalamus. Such a hypothalamic hormone acts as a factor that triggers the release of the gonadotropic hormones, particularly LH. The particular hypothalamic hormone which acts as a releasing factor for the gonadotropins LH and FSH is referred to herein as GnRH, wherein RH stands for "releasing hormone" and Gn signifies that gonadotropin hormones are being released. It is sometimes also referred to as LRF and LHRH. GnRH from mammals, e.g., humans, sheep, pigs, cows, rats, etc., has been previously isolated, identified and synthesized.

Mammalian GnRH has been characterized as a decapeptide having the following structure:

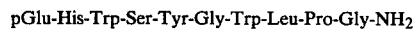
pGlu-His-Trp-Ser-Tyr-Gly-Leu-Arg-Pro-Gly-NH$_2$.

Peptides are compounds which contain two or more amino acids in which the carboxyl group of one acid is linked to the amino group of the other acid. The formula for GnRH, as represented above, is in accordance with conventional representation of peptides where the amino group appears to the left and the carboxyl group to the right. The position of the amino groups is identified by numbering the amino groups from left to right. In the case of GnRH, the hydroxyl portion of the carboxyl group at the right-hand end has been replaced with an amino group (NH$_2$), to give an amide function. The abbreviations for the individual amino acid groups above are conventional and are based on the trivial name of the amino acid: where pGlu is pygroglutamic acid, His is histidine, Trp is tryptophan, Ser is serine, Tyr is tyrosine, Gly is glycine, Leu is leucine, Arg is arginine and Pro is proline. Except for glycine, amino acid residues in the peptides of the invention should be understood to be of the L-configuration unless noted otherwise.

SUMMARY OF THE INVENTION

The present invention provides a purified peptide which exhibits a high potency to cause the release of gonadotropins in fish. The present invention provides a peptide which has a potent effect on the reproduction processes of fish and is termed Fish GnRH. It is a decapeptide that was isolated and purified from thousands of salmon brains and then characterized. The large amount of fish brains was necessitated by the fact that a salmon brain would contain less than about 10 nanograms of this peptide.

DETAILED DESCRIPTION OF THE PREFERRED EMBODIMENT

In accordance with the present invention, the following peptide has been synthesized which is potent to release gonadotropins in fish and is believed to be naturally occurring Fish GnRH:

pGlu-His-Trp-Ser-Tyr-Gly-Trp-Leu-Pro-Gly-NH$_2$

The peptide is synthesized by a suitable method, such as by exclusively solid-phase techniques, by partial solid-phase techniques, by fragment condensation, by classical solution addition or by the employment of recently developed recombinant DNA techniques. For example, the techniques of exclusively solid-state synthesis are set forth in the textbook "Solid-Phase Peptide Synthesis," Stewart and Young, Freeman and Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of the alpha-amino group on an amino acid or a fragment while that entity which is being added reacts at the carboxyl group, followed by the selective removal of the alpha-amino protecting group to allow subsequent reaction to take place at that location.

Among the known classes of α-amino protecting groups are (1) acyl-type protecting groups, such as formyl, trifluoroacetyl, phthalyl, Tos, benzoyl, benzensulfonyl, nitrophenylsulfenyl, tritylsulfenyl, o-nitrophenoxyacetyl, acrylyl, chloroacetyl, acetyl and α-chlorobutyryl; (2) aromatic urethan-type protecting groups, e.g., benzyloxycarbonyl (Z) and substituted benzyloxycarbonyl, such as p-chloro-benzyloxycarbonyl, p-nitrobenzyloxycarbonyl, p-bromobenzyl-oxycarbonyl and p-methoxybenzyloxycarbonyl; (3) aliphatic urethan protecting groups, such as terbutyloxycarbonyl (Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl, triphenylmethyl(trityl) and benzyl; (7) trialkylsilane groups, such as trimethylsilane. The preferred α-amino protecting group is Boc.

Use of the benzhydrylamine resin permits the C-terminal amide function to be obtained directly after the amino acid sequence in the synthesis is complete by cleaving from the resin support to form the glycine amide at the C-terminal portion of the peptide. When the other resins are used, the anchoring bond is the benzylester group which after cleavage of the peptide from the resin support must be converted to the C-terminal amide. The preferred procedure is to ammonolyse the protected peptide off the resin and then remove the protecting group by hydrogenolysis or by hydrogen fluoride cleavage. An alternative procedure is to cleave by transesterification with methanol/(Et)$_3$N and then convert the resulting ester into an amide and subsequently deprotect as described above. See Stewart "Solid-Phase Peptide Synthesis", pages 42-46.

In the Example set forth hereinafter, the α-amino protected amino acids are coupled step-wise in the desired order to obtain a compound of the desired formula; however, as an alternative to adding each amino acid separately to the reaction, some of them may be coupled prior to addition to the solid phase reaction.

After the desired amino acid sequence has been synthesized, the peptide is removed from the resin support by treatment with a reagent, such as hydrogen fluoride, which not only cleaves the peptide from the resin but also cleaves all remaining side chain protecting groups and the α-amino protecting group (if present) on pyroglutamic acid to obtain the peptide directly in the case where the benzhydrylamine resin was used. Where a chloromethylated resin is used, the peptide may be separated from the resin by methanolysis after which the recovered product is chromatographed on silica gel and the collected fraction subjected to ammonolysis to convert the methyl ester to the C-terminal amide. Any side chain-protecting group may then be cleaved as previously described or by other procedures, such as catalytic reduction (e.g., Pd on C) using conditions which will keep the Trp moiety intact. When using hydrogen fluoride for cleaving, anisole is included in the reaction vessel to prevent the destruction of labile amino acid side chain (i.e., tryptophan).

The peptides of the present invention are preferably synthesized by a solid phase technique using a chloromethylated resin, a methylbenzhydrylamine resin (MBHA) or a benzhydrylamine (BHA) resin. The synthesis is conducted in a manner to stepwise add the amino acids in the chain in the manner set forth in detail in the U.S. Pat. No. 4,211,693, the disclosure of which is incorporated herein by reference. Side-chain protecting groups, as are well known in the art, are added to Ser, Tyr and His before these amino acids are coupled to the chain being built up upon the resin. A side-chain protecting group may also be added to Trp although often times Trp is used without side-chain protection when solid phase synthesis is used.

Solid-phase synthesis provides the fully protected intermediate peptidoresin. The fully protected peptide can be cleaved, for example, from a chloromethylated resin support by ammonolysis to yield the fully protected amide intermediate. The intermediate of the invention may be represented as: $X^1$-pGlu-His($X_6^2$)-Trp($X^3$)-Ser($X^4$-Tyr($X^5$)-Gly-Trp($X^3$)-Leu-Pro-Gly-$X^6$ wherein:

$X^1$ is hydrogen or an α-amino protecting group of the type known to be useful in the art in the stepwise synthesis of polypeptides for the α-amino nitrogen of pGlu, such as one from the group (2) set forth hereinbefore, and preferably is Z when one is employed.

$X^2$ is a protecting group for the imidazole nitrogen of His and is selected from the group consisting of 2,4-dinitrophenyl, Boc, benzyl, Z and Tos; alternatively $X^2$ may be hydrogen, which means there is no protecting group on the side chain nitrogen atom.

$X^3$ is hydrogen or a protecting group, for the indole nitrogen, such as formyl or benzyl; however in many syntheses there is no need to protect Trp.

$X^4$ is a protecting group for the alcoholic hydroxyl group of Ser and is selected from the group consisting of acetyl, benzoyl, tetrahydropyranyl, tert-butyl, trityl, benzyl and 2,6-dichlorobenzyl. Benzyl is preferred. Alternatively $X^4$ may be hydrogen.

$X^5$ is a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl, the latter being preferred. Alternatively $X^5$ may be hydrogen.

$X^6$ is NH$_2$, —O—CH$_2$—[resin support], —NH—[resin support], ester, amide or hydrazide.

The criterion for selecting side chain protecting groups for $X^2$-$X^5$ is that the protecting group should be stable to the reagent under the reaction conditions selected for removing the α-amino protecting group at each step of the synthesis. The protecting group should not be split off under coupling conditions, and the protecting group must be removable upon completion of the synthesis of the desired amino acid sequence under reaction conditions that will not alter the peptide chain.

When the $X^6$ group is —O—CH$_2$—[resin support], the ester moiety of one of the many functional groups of the polystyrene resin support is being represented. When the $X^6$ group is Gly-NH-[resin support], an amide bond connects Gly to BHA resin or to a methyl BHA resin.

Deprotection of the peptides as well as cleavage of the peptide from the benzhydrylamine resin preferably takes place at 0° C. with hydrofluoric acid (HF). Anisole is added to the peptide prior to treatment with HF. After the removal of HF, under vacuum, the cleaved, deprotected peptide is treated with ether, decanted, taken in dilute acetic acid and lyophilized.

Purification of the peptide is effected by ion exchange chromatography on a CMC column, followed by partition chromatography using the elution system: n-butanol: 0.1 N acetic acid (1:1 volume ratio) on a column packed with Sephadex G 25. The peptide of the invention is effective at a level of less than about 10 micrograms per 100 grams of body weight, when administered to fish. It is considered to be effective in fish and in other vertebrates, including mammals and amphibians.

EXAMPLE

The following peptide having the formula pGlu-His-Trp-Ser-Tyr-Gly-Trp-Leu-Pro-Gly-NH$_2$ is prepared by the solid phase procedure referred to above.

A BHA resin is used, and Boc-protected Gly is coupled to the resin over a 2-hour period in CH$_2$Cl$_2$ using a 3-fold excess of Boc derivative and DCC as an activating reagent. The glycine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 10 |
| 5 | $CH_2Cl_2$ wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |
| 10 | MeOH wash-40 ml. (2 times) | 3 |
| 11 | TEA 12.5 percent in $CH_2Cl_2$-70 ml. (1 time) | 3 |
| 12 | MeOH wash-30 ml. (2 times) | 3 |
| 13 | $CH_2Cl_2$ wash-80 ml. (2 times) | 3 |

After step 13, an aliquot is taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. N αBoc protection is used for each of the remaining amino acids throughout the synthesis. The side chain of His is protected with Tos, but the side chain of Trp is not protected. OBzl is used as a side chain protecting group for the hydroxyl group of Ser, and 2-6 dichlorobenzyl is used as the side chain protecting group for the hydroxyl group of Tyr. pGlu protected by Z is introduced as the final amino acid. Boc-Trp has low solubility in $CH_2Cl_2$ and is coupled using DMF.

The cleavage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by semi-preparative reverse phase HPLC as described in Rivier et al. *Peptides: Structure and Biological Function* (1979) pp. 125-128. Purity is checked, and if the desired purity is not obtained, further purification is carried out by RP-HPLC using an acetonitrile gradient in 0.1% TFA.

The decapeptide is judged to be homogenous using thin layer chromatography and several different solvent systems, as well as by using reversed phase, high-pressure liquid chromatography and an aqueous triethylammonium phosphate solution, plus acetonitrile. Amino acid analysis of the resultant purified peptide is consistent with the formula for the prepared structure, showing substantially integer values for each amino acid chain. The optical rotation is measured on a photoelectric polarimeter $[\alpha]_D^{22} = -39°$ (C=1, 1% acetic acid).

The frog has two GnRH-like peptides. In the adult frog brain, a peptide has been identified which is identical to mammalian GnRH; however, in the neonatal brain and in spinal ganglion, a different peptide is present, which is now believed may have the same structure as Fish GnRH. It is also likely that the mammalian nervous system has a similar counterpart which is active within the central nervous system to modify sexual behavior.

The peptide prepared in the Example is assayed in vitro using cultures of living superior cervical ganglian cells recently removed from frogs. Equivalent cultures are treated with an amount of Fish GnRH and with the same and greater amounts of mammalian GnRH. These cultures are then compared with controls. Shortly following treatment, the cultures are tested by making intracellular recordings which are indicative of ion movement through the cell membranes. The results of this specific assay show that the Fish GnRH synthetic peptide is about 10 times more potent than mammalian GnRH.

It is believed that the peptide can be used to regulate fertility in fish, and more particularly, it is expected to have substantial practical value in promoting spawning of teleostei fish of a wide variety of species, with immediate use being seen in fish hatcheries. In this respect, it is contemplated that administration may be by peritoneal or intramuscular injection to fish at a dosage between about 20 μg. and about 100 μg. or less for fish having a body weight of about 100 grams. It is also felt that the peptide may be administered by dissolving in water in which fish swim for a predetermined period during which the peptide will be absorbed into the bloodstream of the fish via the gills.

A peptide of this type is often administered in the form of a veterinarily or pharmaceutically acceptable, nontoxic salt, such as an acid addition salt or a metal complex, e.g., with zinc, iron, calcium, barium, magnesium, aluminum or the like (which is considered as an addition salt for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like.

The peptide or a nontoxic salt thereof, combined with a pharmaceutically acceptable carrier to form a pharmaceutical composition, may also be administered to mammals, including humans, where it has shown in vitro potency, either intravenously, subcutaneously, intramuscularly, intranasally, intracerebrospinally or orally. For adminstration to humans, the peptide should be at least about 93% pure and preferably should have a purity of at least about 98%. This purity means that the intended peptide constitutes the stated weight % of all like peptides and peptide fragments present. Administration may be employed by a physician or by a veterinarian to regulate the secretion of gonadotropins and/or to cause ovulation. The required dosage will vary with the particular objective to be achieved with the duration of desired treatment. Generally, dosages similar to those used with mammalian GnRH may be employed, wherein individual dosages between about 5 ng. and about 1 μg. per kilogram of body weight may be used. At present time, the primary field of use is expected to be in teleostei fish where it may be used at far lower purity, e.g. at about 5% purity or even as low as about 1% purity. As previously indicated, the natural decapeptide is present in such fish in only minute amounts so that an initial extract from such fish would contain far less than 1% of such decapeptide.

Although the invention has been described with regard to its preferred embodiment, it should be understood that changes and modifications as would be obvious to one having the ordinary skill in this art may be made without departing from the scope of the invention which is set forth in the claims appended hereto.

Various features of the invention are emphasized in the claims which follow:

What is claimed is:

1. A peptide composition consisting essentially of a peptide having the formula:

pGlu-His-Trp-Ser-Tyr-Gly-Trp-Leu-Pro-Gly-NH$_2$.

2. A peptide in accordance with claim 1, in the form of a nontoxic salt thereof.

3. A method of promoting the spawning of fish by administering an effective amount of pGlu-His-Trp-Ser-Tyr-Gly-Trp-Leu-Pro-Gly-NH$_2$.

4. A method in accordance with claim 3 wherein said administering is by injection.

5. A method in accordance with claim 4 wherein a dosage of not more than about 100 μg is administered for each 100 g. of fish body weight.

6. A method in accordance with claim 3 wherein said administering is by dissolving in water wherein the fish are swimming.

7. A non-toxic salt of the peptide of claim 1.

* * * * *